United States Patent [19]

Umezawa et al.

[11] Patent Number: 4,914,192
[45] Date of Patent: Apr. 3, 1990

[54] MYCAMINOSYL TYLONOLIDE DERIVATIVES

[75] Inventors: Hamao Umezawa, Tokyo; Sumio Umezawa, Tokyo; Tsutomu Tsuchiya, Kanagawa; Tomio Takeuchi, Tokyo; Akihiro Tanaka, Tokyo; Shuichi Sakamoto, Tokyo, all of Japan

[73] Assignee: Yamanouchi Pharmaceutical Co., Ltd., Tokyo, Japan

[21] Appl. No.: 244,500

[22] Filed: Sep. 14, 1988

Related U.S. Application Data

[62] Division of Ser. No. 861,537, May 9, 1986, Pat. No. 4,794,173.

[30] Foreign Application Priority Data

May 13, 1985 [JP] Japan .................. 60-102402

[51] Int. Cl.$^4$ ............................ C07H 17/08
[52] U.S. Cl. ................................ 536/7.1
[58] Field of Search ............ 536/7.1; 514/30

[56] References Cited

U.S. PATENT DOCUMENTS

| | | | |
|---|---|---|---|
| 4,345,069 | 8/1982 | Sakakibara et al. | 536/7.1 |
| 4,415,730 | 11/1983 | Fujiwara et al. | 536/7.1 |
| 4,421,911 | 12/1983 | Fujiwara et al. | 536/7.1 |

FOREIGN PATENT DOCUMENTS 0042697  3/1982  Japan .................. 536/7.1

*Primary Examiner*—Johnnie R. Brown
*Assistant Examiner*—Elli Peselev
*Attorney, Agent, or Firm*—Burgess, Ryan & Wayne

[57] ABSTRACT

Mycaminosyl tylonolide derivatives represented by the following general formula

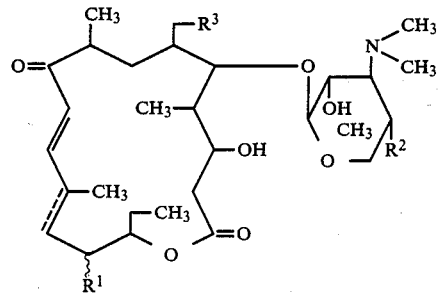

(wherein $R^1$ denoted hydroxyl group, a lower alkanoyloxy group, benzyloxy group, azido group, or amino group which may optionally be substituted with a lower alkyl or a lower alkanoyl radical; $R^2$ stands for hydrogen atom or hydroxyl group; $R^3$ expresses hydrogen atom or formyl group; and ==== means a double bond or a radical represented by

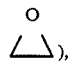

and salts thereof.

5 Claims, No Drawings

MYCAMINOSYL TYLONOLIDE DERIVATIVES

This is a division of application Ser. No. 861,537, filed May 9, 1986, now U.S. Pat. No. 4,794,173.

BACKGROUND OF THE INVENTION

Various mycaminosyl tylonolide derivatives have been known so far. However, mycaminosyl tylonolide derivatives are not known wherein an unsubstituted or substituted amino group, etc. is directly attached to the 14-position of the derivatives.

The compounds of this invention are novel compounds having excellent antibacterial activity, and have a characteristic in that the 14-position has a substituent selected from a hydroxyl group, a lower alkanoyloxy group, benzoyloxy group, azido group, or amino group which may optionally be substituted with a lower alkyl group or a lower alkanoyl group.

The subject matter of this invention is directed to such particular novel compounds, and the production methods for the compounds. The compounds also include the salts thereof such as acid addition salts.

DETAILED EXPLANTION OF THE INVENTION

Technical Field

This invention relates to macro-lactone compounds having a broad spectrum of antibacterial activity against Gram-positive and -negative bacteria. More particularly, it relates to new 14-substituted mycaminosyl tylonolide derivatives represented by the following general formula (I)

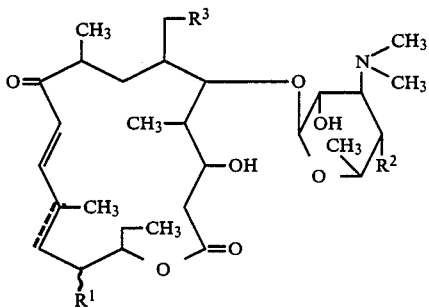

(wherein $R^1$ denotes hydroxyl group, a lower alkanoyloxy group, benzyloxy group, azide group, or amino group which may optionally be substituted with an lower alkyl or a lower alkanoyl radical; $R^2$ stands for hydrogen atom or hydroxyl group; $R^3$ express hydrogen atom or formyl group; and === means a double bond or a radical represented by

), and salts thereof.

Description of the Prior Art

A large number of patents have been filed on mycaminosyl tylonolide derivatives. For example, U.S. Pat. No. 4,433,109 filed by the present inventors discloses a wide variety of compounds in which the 23-position carbon of the macro-lactone ring has substituent groups such as hydroxyl, alkanoyloxy radicals and arylcarbonyloxy radicals; and European Patent Application (Laid-open) No. 70,170 also filed by the present inventors discloses compounds in which substitutent groups at the 23-position carbon in the macro-lactone ring are hydroxyl, halogen atoms and radicals represented by

(wherein $R_a$ is hydrogen atom or a lower alkyl which may optionally be substituted with hydroxyl group, and $R_b$ is hydrogen atom, aryl, aralkyl or a lower alkyl, aryl or aralkyl which may optionally be substituted with hydroxyl group).

However, the compounds of this invention are distinctly different in structure from the compounds mentioned above; the compounds of this invention are new mycaminosyl tylonolide derivatives and salts thereof which have never been found in nature, are very difficult to synthesize, and are characterized in that hydroxyl group, a lower alkanoyloxy group, benzoyloxy group, azido group, or amino group which may optionally be substituted with a lower alkyl or a lower alkanoyl radical, is directly attached to the 14-position.

In addition, the compounds of this invention have a broad spectrum of antibacterial activity against Gram-positive and -negative bacteria as detailed below.

Illustrative Examples of the Objective Compounds

The compounds defined by the general formula (I) shown above will be described below in more detail. "Lower alkyl groups" herein mean linear or branched alkyl groups of 1 to 6 carbon atoms, such as methyl, ethyl, n-propyl, isopropyl, n-butyl, isobutyl, tert-butyl and n-pentyl.

"Lower alkanoyl groups" herein mean linear or branched alkanoyl groups of 1 to 6 carbon atoms, such as acetyl, propionyl, isopropionyl, butyryl, tert-butyryl and valeryl; and "lower alkanoyloxy groups" herein mean radicals in which oxygen atom has been attached to the carbonyl of "lower alkanoyl groups", such as acetoxy, propionyloxy, isopropionyloxy, butyryloxy, t-butyryloxy, valeryloxy and hexanoyloxy.

"Amino groups which may optionally be substituted with a lower alkyl or lower alkanoyl group" include unsubstituted amino, methylamino, dimethylamino, ethylamino, ethylmethylamino, diethylamino, propylamino, isopropylamino, butylamino, butylmethylamino, acetamide, butyramide and pentanamide groups.

Each of the compounds of this invention (having an asymmetric carbon at 14-position of the macro-lactone ring) exists in two stereoisomeric forms depending on whether the substituent group $R^1$ at 14-position is attached in α- or β-conformation. It is needless to say that all these stereoisomers and mixtures thereof are included in the scope of this invention.

The macro-lactone compounds of this invention form salts with various acids, etc. These acids include inorganic acids such as hydrochloric, hydrobromic, hydroiodic, sulfuric, nitric and phosphoric acids, and organic acids such as formic, acetic, oxalic, citric, succinic, maleic, malic, tartaric, methanesulfonic, toluenesulfonic acid and ethanesulfonic acids. The salts of these acids can be prepared by usual methods.

The compounds of this invention (I) have a broad anti-bacterial spectrum against Gram-positive and -negative bacteria. Those having dimethylamino groups at 14-position in α-conformation, in particular, exhibit powerful activity against Gram-negative bacteria.

The table given on next page lists minimum growth-inhibition concentrations of compounds (I) against various bacteria.

TABLE

| | (Minimum Growth-Inhibition Concentrations, γ/ml) | | | | | | |
|---|---|---|---|---|---|---|---|
| | | Example No. | | | | | |
| Strain | MT | 1 | 2 | 3 | 5 | 6 | 7 |
| B. Subtilis NRRL B-558 | 3.12 | 3.12 | <0.2 | 0.39 | <0.2 | 0.78 | 0.78 |
| M. luteus PCI 1001 | <0.2 | <0.2 | <0.2 | <0.2 | <0.2 | 0.2 | <0.2 |
| Staph. aureus Smith | 1.56 | 0.78 | 0.39 | 0.39 | 0.78 | 0.78 | 0.39 |
| E. coli K-12 | 25 | 12.5 | 12.5 | 12.5 | 12.5 | 6.25 | 3.12 |
| Kl. pneumoniae PCI-602 | 3.12 | 1.56 | 12.5 | 12.5 | 3.12 | 3.12 | 1.56 |
| Sal. entiritidis 1891 | 3.12 | 1.56 | 3.12 | 3.12 | 3.12 | 0.78 | 1.56 |

MT: Micaminosyl Tylonolide

The desired compounds of this invention (I) can be prepared by any of the methods described below.

PROCESS 1

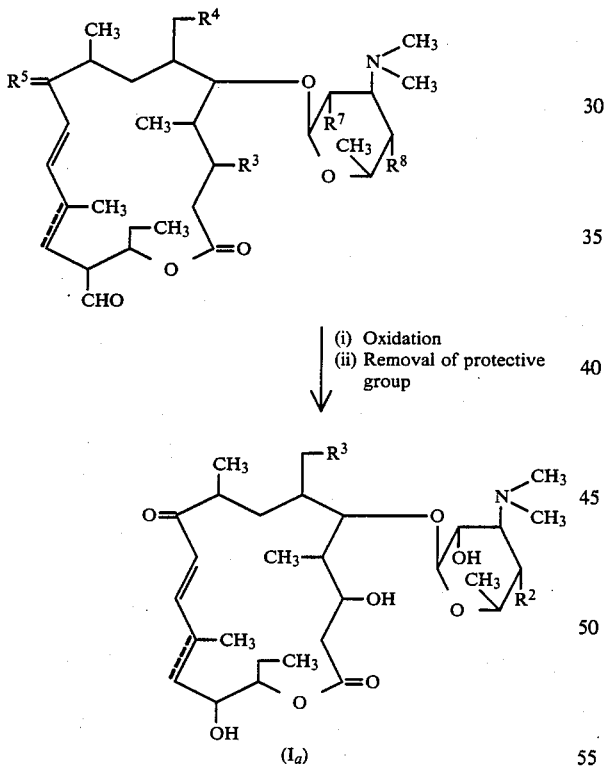

(wherein $R^4$ is hydrogen atom or formyl group which may optionally be protected, $R^5$ is oxygen atom or a protective group for carbonyl; $R^6$ is hydrogen atom or hydroxyl which may optionally be protected; $R^7$ and $R^8$ are each hydroxyl which may optionally be protected; and $R^2$, $R^3$ and ═══ are as defined above).
Preferable protective groups are as follows:
Protective groups for formyl at $R^4$ and for carbonyl at $R^5$:

Acetals, thioacetals, ketals and thioketals, such as dimethylacetal, diethylacetal, diethylthioacetal, ethyleneacetal, ethylenethioacetal, propyleneacetal, dimethylketal, diethylketal, diethylthioketal, ethyleneketal, ethylenethioketal and propyleneketal.
Protective groups for hydroxyls at $R^6$ and $R^7$:

Lower acyls, such as acetyl, propionyl, butyryl, valeryl and isovaleryl.
Protective groups for hydroxyl at $R^8$:

tert-Butyldimethylsilyl, 2-tetrahydropyranyl and 2-tetrahydrofuranyl.

This process involves two steps: (i) oxidation of the formyl group at 14-position of starting material (II) to form 14-formoxy-3'-dimethylaminooxide compound, and then (ii) reducing the formed compound in order to convert 14-formoxy to 14-hydroxy and to change the 3'-dimethylaminooxide to 3'-dimethylamino, and then, if any protective group is present, removing protective group(s).

(i) The oxidation of the starting material (II) can be carried out in a conventional manner. That is, it can be carried out preferably by using an oxidation agent such as peroxy acid (for example, meta-chloro perbenzoic acid, peracetic acid, etc.). It is preferable to add an inorganic alkaline salt (for example, sodium hydrogen carbonate, potassium hydrogen carbonate, sodium acetate, etc.) for the purpose of inhibiting side reactions. The oxidation can be carried out preferably in organic solvent such as chloroform, dichloromethane, etc.

(ii) Removal of the protective groups for the hydroxyls at $R^6$ and $R^7$ may be easily effected by heating in methanol, an aqueous alcohol or an aqueous aprotic solvent. The protective groups for the formyl at $R^4$, and for the carbonyl at $R^5$ can be removed by treatment with a mineral acid, such as hydrochloric and sulfuric acids, or an organic acid, such as acetic, trifluoroacetic and trichloroacetic acids. The protective group for the hydroxyl at $R^8$ can be removed by treatment with tetrabutylammonium fluoride or potassium fluoride, etc., namely in neutral condition, or can be removed together with the protective groups for formyl at $R^4$ and the carbonyl at $R^5$ by treatment with a mineral acid (such as hydrochloric acid and sulfuric acid) or organic acid (such as acetic, trifluoroacetic and trichloroacetic acids).

PROCESS 2

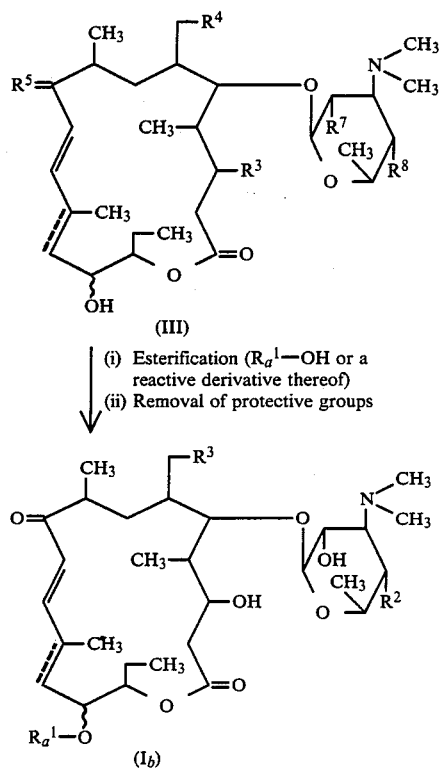

(i) Esterification ($R_a^1$—OH or a reactive derivative thereof)
(ii) Removal of protective groups

PROCESS 3

Compound (III)
Azide formation

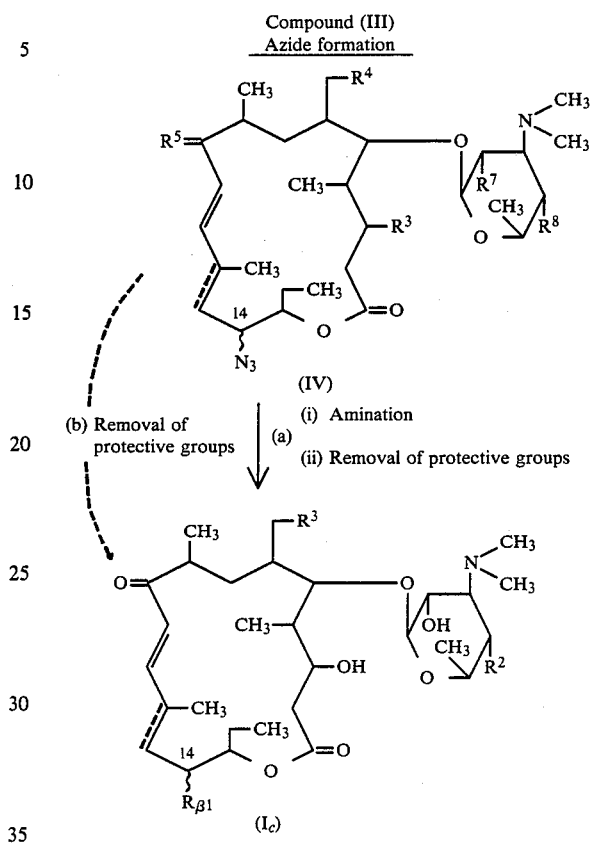

(b) Removal of protective groups
(a) (i) Amination
(ii) Removal of protective groups (wherein $R^1$ is a lower alkanoyl or benzoyl group; $R^4$ is hydrogen atom or formyl which may optionally be protected; $R^2$, $R^3$, ===, $R^5$, $R^6$, $R^7$ and $R^8$ are as defined above.

This process involves two steps: (i) esterifiction of the hydroxyl group at 14-position of starting material (III), and (ii) removal of protective groups if any.

Step (i):

Esterification of starting materials (III) may be effected by any known technique; preferably, by reaction with an acid anhydride (e.g., acetic anhydride, valeric anhydride and butyric anhydride) or an acid halide (e.g., acetyl chloride, propionyl chloride, butyryl chloride and benzoyl chloride) in an organic solvent such as pyridine and diethylamine, etc. The DCC process (reaction of free carboxylic acids in pyridine or pyridinedimethylaminopyridine in the presence of dicyclohexylcarbodiimide) may also be adopted.

The esterification may also be effected by reacting formic acid, acetic acid, propionic acid, valeric acid, etc. (that is, free carboxylic acid, itself) in the presence of diethyl azodicarboxylic acid, triphenylphosphine, etc. in a solvent such as dry toluene, dry oxolane, etc. In this case, the 14-conformation at 14-position in the case of the starting material.

Step (ii)

Removal of protective group(s) may be effected in the manner similar to that at ii) in the before-mentioned Process 1.

(wherein $R^1$ is azide or amino group which may optionally be substituted with a lower alkyl or lower alkanoyl radical; and $R^2$, $R^3$, ---, $R^4$, $R^5$, $R^6$, $R^7$ and $R^8$ are as defined above).

This process also involves two reaction steps: (1) azide formation at 14-position, and (2) (a) amination, followed by removal of protective groups if any, or (b) direct removal of protective groups from the azide compounds.

Azide formation in step (1) is preferably carried out by reaction with azidodiphenylphosphoryl (or hydrazoic acid) in a solvent, such as anhydrous toluene and oxolane, in the presence of diethyl azodicarboxylate and triphenylphosphine.

Amination in step (2) can be easily effected by treatment of an azide compound (IV) with triphenylphosphine and water in a solvent such as oxolane and acetonitrile. It is possible, when desired, to introduce a lower alkyl or lower alkanoyl group to the amino compound thus obtained.

Introduction of a lower alkyl group, for example, may be achieved by reaction with an aldehyde (e.g., paraformaldehyde, acetaldehyde and propionaldehyde) in anhydrous methanol at room temperature or at an elevated temperature, followed by reduction with sodium cyanoborohydride, sodium borohydride or the like.

Lower alkanoyl groups can be introduced by reaction with an acid halide or acid anhydride (e.g., methyl chloroformate, ethyl chloroformate, acetyl chloride, propionyl chloride and acetic anhydride.

Removal of the protective groups can be effected in the same manner as in Process 1.

PROCESS 4

Compound (III)

(Step 1) ↓ Introduction of leaving groups (Step 2) ↓ (i) Substitution reaction
(ii) Removal of protective groups

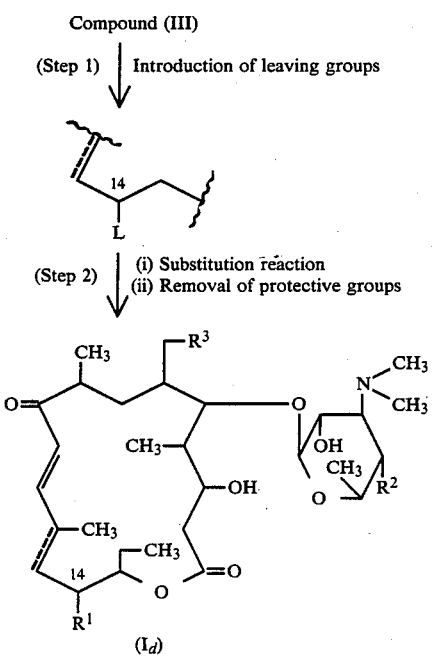

(I_d)

(wherein L is a leaving group; and $R^1$, $R^2$, $R^3$ and ≡≡≡ are as defined above).

This process consists of two steps: introducing a suitable leaving group to the C-14 hydroxyl in starting material (III) (Step 1), and subsequent substitution reaction (Step 2).

Preferable leaving groups to be introduced in Step 1 are organic sulfonic acid residues, such as tosyl and mesyl groups. These groups may be easily introduced by reaction of corresponding halides (e.g., tosyl chloride and mesyl chloride) in a solvent such as pyridine and triethylamine.

The reaction conditions of Step 2 are properly selected depending on the type of substituting group; for example, sodium azide, sodium acetate, alkylamines and sodium alcoholates are generally subjected to reaction in a solvent such as dimethylformamide and acetonitrile. Removal of the protective groups may be effected in the same manner as in Process 1.

OTHER PROCESSES (A) Deformylation at 19-position

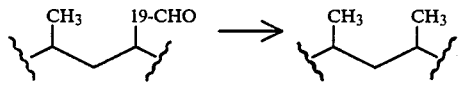

This process involves removal of formyl group at 19position in mycaminosyl tylonolide derivatives. The reaction is preferably carried out by the action of chlorotris(triphenylphosphine)rhodium in an organic solvent, such as benzene and toluene, at room temperature or at an elevated temperature.

(B) Epoxidation at 12,13-double bond

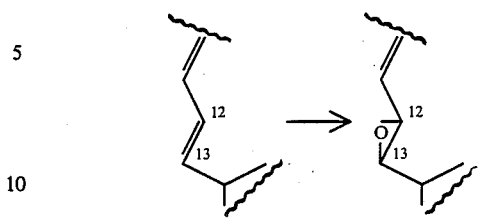

This process involves epoxidation at 12,13-double bond in mycaminosyl tylonolide derivatives. The reaction is preferably carried out by the action of m-chloroperbenzoic acid under cooling or under heating, followed by treatment with an acid.

(C) Dehydroxylation at 4'-position

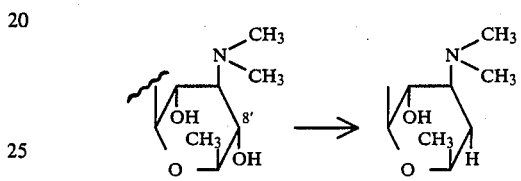

This process involves conversion of the hydroxyl at 4'-position in mycaminosyl tylonolide derivatives into hydrogen. The reaction is preferably carried out by the action of benzylsulfonium chloride in a solvent, such as pyridine, at a temperature of $-40°$ to $-30°$ C., followed by treatment with sodium iodide and tributyltin hydride in that order.

These reactions, (A), (B) and (C), may be adopted, as required, before, during or after any of Processes 1 through 4 described above.

As stated earlier, each of the compounds of this invention exists in two stereoisomeric forms ($\alpha$- and $\beta$-isomers at 14-C). In these isomers, the steric configuration can be inverted by the action of an organic acid (e.g., formic and acetic acids), hydrazoic acid or azidodiphenylphosphoryl, etc.—the method of Mitsunobu (Oyo Mitsunobu: Synthesis, 1981, 1–28). Hence, the esterification in Process 2 in the case of using diethyl azodicarboxylyl and triphenylphosphine as well as the azide formation reaction in Process 3 by using azidodiphenylphosphoryl, which is no other than the reaction of the above Mitsunobu method, is accompanied by inversion of steric configuration at 14-position ($\alpha$- to $\beta$-conformation, or vice versa).

It is also known that the substituent reaction in Process 4 is generically accompanied by inversion of steric configuration.

One may thus understand that, in the process of this invention, a desired compound having a desired steric configuration at 14-position can be obtained by using a starting material having 14-hydroxyl group of a specific configuration.

The reaction products obtained by the processes described above are treated by extraction with organic solvents, recrystallization, filtration, reprecipitation, column chromatography and other known techniques, giving pure products.

The pure compounds (i) thus obtained may be formed into tablets, powder, granules, capsules, injections and other pharmaceutical preparations for oral and parenteral administration. Suitable daily dose is 10 mg. to 1000 mg (given once to four times a day); that is, a daily total of 10 to 1,000 mg is usually administered in one to four doses.

The following examples further detail the preparative methods of the compounds of this invention. Some of the starting materials used for the synthesis thereof are novel compounds, so their manufacturing methods are also shown in the following Reference Examples.

Compounds of Examples

[Chemical structure diagram with substituents $R^1$, $R^2$, $R^3$]

| Ex. No. | $R^1$ | $R^2$ | $R^3$ | — |
|---|---|---|---|---|
| 2 | β-CH$_2$COO— | OH | CHO | = |
| 3 | β-(CH$_3$)$_2$CHCH$_2$COO— | " | " | " |
| 4 | β-CH$_3$CH$_2$COO— | " | " | " |
| 5 | β-⟨phenyl⟩-COO— | " | " | " |
| 6 | α-(CH$_3$)$_2$N— | " | " | " |
| 7 | α-(CH$_3$)$_2$N— | H | " | " |
| 8 | α-CH$_3$COO— | OH | " | " |
| 9 | α-CH$_3$CH$_2$COO— | " | " | " |
| 10 | β-(CH$_3$)$_2$N— | " | " | " |
| 12 | α-CH$_3$CO—NH— | " | " | " |
| 13 | α-(CH$_3$)$_2$N— | H | H | " |
| 14 | α-(CH$_3$)$_2$N— | " | CHO | O⟨epoxide⟩ |
| 1 | β-OH | OH | CHO | = |
| 11 | α-OH | " | " | " |

REFERENCE EXAMPLE 1

Mycaminosyl tylonolide diethylacetal (38.5 g) was dissolved in a mixture of 800 ml benzene and 200 ml sulfolane, ethylene glycol (37 ml), pyridine p-toluenesulfonate (18 g) and p-toluenesulfonic acid (5.5 g) were added, and the resulting mixture was heated under reflux for 48 hours according to the method of Tsuchiya [Jpn. J. Antibiotics, 32(Suppl.) (1979), S129-135]. The reaction mixture was poured into an aqueous saturated solution of sodium bicarbonate, and the mixture was extracted separately with benzene and chloroform. Each organic layer was treated as usual, the solvent was distilled off, and the residue was purified by silica gel column chromatography (chloroform/methanol/28%-ammonia: 30/1/0.1 ~ 18/1/0.1), giving pure mycaminosyl tylonolide 9,20-diethyleneacetal (yield: a total of 24.4 g). It showed the following properties:

$[\alpha]_D^{20} + 12°$ (c1, CHCl$_3$).

| NMR spectrum (CDCl$_3$): | | |
|---|---|---|
| δ (ppm) | Number of H | Assignment |
| 1.76 | 3H | Me-22 |
| 2.50 | 6H | NMe$_2$ |
| 5.75 | 1H | H-10 |
| 6.36 | 1H | H-11 |

REFERENCE EXAMPLE 2

Acetic anhydride (5.6 g) was added to a solution of mycaminosyl tylonolide 9,20-diethyleneacetal (17.2 g) in 172 ml acetonitrile, and the mixture was kept stirred overnight. After concentrating the reaction mixture, the residue was extracted with benzene, and the extract was worked up as usual, affording 17.4 g of 2',4'-di-O-acetylmycaminosyl tylonolide 9,20-diethyleneacetal as solid. It showed the following properties:

$[\alpha]_D^{22} - 17°$ (c1, CHCl$_3$).

| NMR spectrum (CDCl$_3$): | | |
|---|---|---|
| δ (ppm) | Number of H | Assignment |
| 1.75 | 3H | Me-22 |
| 2.01 | 3H | Ac |
| 2.05 | 3H | Ac |
| 2.34 | 6H | NMe$_2$ |
| 4.65 | 1H | H-1' |

REFERENCE EXAMPLE 3

Tert-butylchlorodimethylsilane (17 g) was added to a solution of 17.4 g 2',4'-di-O-acetylmycaminosyl tylonolide 9,20-diethyleneacetal and 9.2 g imidazole in 140 ml N,N-dimethylformamide, and the mixture was heated at 80° C. for nine hours. After concentrating the reaction mixture, the residue was extracted with benzene, and the extract was worked up as usual, affording 22 g of 2',4'-di-O-acetyl-3,23-di-O-tert-butyldimethylsilylmycaminosyl tylonolide 9,20-diethyleneacetal as solid. It showed the following properties:

| NMR spectrum (CDCl$_3$): | | |
|---|---|---|
| δ (ppm) | Number of H | Assignment |
| 1.71 | 3H | Me-22 |
| 2.05, 2.06 | 3H | Ac × 2 |
| 2.35 | 6H | NMe$_2$ |
| 4.45 | 1H | H-1' |

$[\alpha]_D^{22} - 58°$ (c1, CHCl$_3$).

REFERENCE EXAMPLE 4

1 m solution of tetrabutylammonium fluoride in oxolane (20 ml) was added to a solution of 22 g 2',4'-di-O-acetyl-3,23-di-O-tert-butyldimethylsilylmycaminosyl tylonoli 9,20-diethyleneacetal in 220 ml oxolane, and the mixture was allowed to stand at room temperature for two hours. After concentrating the reaction mixture, the residue was extracted with benzene, the extract was worked up as usual, the solvent was distilled off, and the residue was purified by silica gel chromatography (toluene/ethyl acetate: 1/1 1/2), giving 16 g of pure 2',4'-di-acetyl-3-O-tertbutyldimethylsilylmycaminosyl tylonolide 9,20-diethyleneacetal as solid. It showed the following properties:

$[\alpha]_D^{20} -54°$ (c1, CHCl$_3$).

| NMR spectrum (CDCl$_3$): | | |
|---|---|---|
| δ (ppm) | Number of H | Assignment |
| 0.89 | 9H | Si-tBu |
| 1.75 | 3H | Me-22 |
| 2.05, 2.06 | 3H | Ac × 2 |
| 2.34 | 6H | NMe$_2$ |
| 4.44 | 1H | H-1' |

REFERENCE EXAMPLE 5

2',4'-di-O-acetyl-3-O-tert-butyldimethylsilylmycamin tylonolide 9,20-diethylacetal (5.02 g) was dissolved in a mixture of 25 ml benzene and 25 ml dimethylsulfoxide, 1.67 g of pyridinium trifluoroacetate and 2.37 g of N,N'-dicyclohexylcarbodiimide were added in that order, and the resulting mixture was kept stirred at room temperature overnight. The reaction mixture was poured into a solution of 0.97 g oxalic acid dihydrate in 20 ml dioxane, the precipitate was filtered off, and the filtrate was concentrated. The residue was dissolved in benzene, the solution was worked up as usual, and the solvent was distilled off, affording 4.7 g of 2',4'-di-O-acetyl-3-O-tert-butyldimethylsilyl-23-deoxy-23-oxomycaminosyl tylonolide 9,20-diethyleneacetal as solid. It showed the following properties:

$[\alpha]_D^{20} -35°$ (c2, CHCl$_3$).

| NMR spectrum (CDCl$_3$): | | |
|---|---|---|
| δ (ppm) | Number of H | Assignment |
| 2.34 | 6H | NMe$_2$ |
| 5.49 | 1H | H-14 |
| 8.03 | 1H | OCHO |

REFERENCE EXAMPLE 6

Sodium bicarbonate (1.4 g) was added to a solution of 4.7 g 2',4'-di-O-acetyl-3-O-tert-butyldimethylsilyl-23-deoxy-23-oxomycaminosyl tylonolide 9,20-diethyleneacetal in 90 ml chloroform, 3.01 g of m-chloroperbenzoic acid was further added at room temperature, and the mixture was stirred for three hours. The reaction mixture was extracted with chloroform, the organic layer was worked up as usual, and the solvent was distilled off. The residue was then dissolved in toluene, 4.2 ml triphenyl phosphite was added to the solution, and the mixture was kept stirred overnight at room temperature. The reaction mixture was subjected to silica gel column chromatography (toluene/ethyl acetate: 3/1), giving 1.22 g of 2',4'-di-O-acetyl-3-O-tert-butyldimethylsilyl-14-dehydroxymethyl-14-β-formoxymycaminosyl tylonolide 9,20-diethyleneacetal as solid. It showed the following properties:

$[\alpha]_D^{20} -35°$ (c2, CHCl$_3$).

| NMR spectrum (CDCl$_3$): | | |
|---|---|---|
| δ (ppm) | Number of H | Assignment |
| 2.34 | 6H | NMe$_2$ |
| 5.49 | 1H | H-14 |
| 8.03 | 1H | OCHO |

REFERENCE EXAMPLE 7

A solution of 1.2 g 2',4'-di-O-acetyl-3-O-tert-butyl-dimethylsilyl-14-dehydroxymethyl-14-α-formoxymycaminosyl tylonolide 9,20-diethyleneacetal in 24 ml methanol was heated at 50° overnight with stirring. After concentrating the reaction mixture, the residue was purified by silica gel column chromatography (chloroform/methanol/28%-ammonia: 30/1/0.1 10/1/0.1), affording 1.06 g of 3-O-tert-butyl-dimethylsilyl-14-dehydroxymethyl-14-β-hydroxymycaminosyl tylonolide as solid. It showed the following properties:

| NMR spectrum (CDCl$_3$): | | |
|---|---|---|
| δ (ppm) | Number of H | Assignment |
| 1.78 | 3H | Me-22 |
| 2.52 | 6H | NMe$_2$ |
| 5.51 | 1H | H-13 |
| 5.73 | 1H | H-10 |
| 6.35 | 1H | H-11 |

What is claimed is:

1. Mycaminosyl tylonolide derivatives represented by the formula:

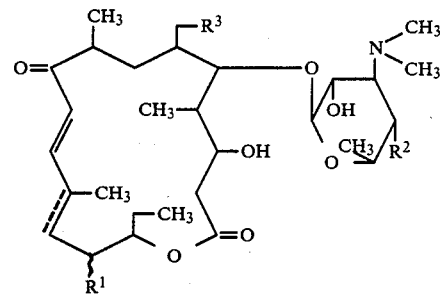

wherein R$^1$ represents a hydroxyl group; R$^2$ represents hydrogen or a hydroxyl group; R$^3$ represents hydrogen or a formyl group; and === represents

and salts thereof.

2. Mycaminosyl tylonolide derivative and salts thereof as claimed in claim 1 wherein R$^2$ and R$^3$ represent hydrogen.

3. Mycaminosyl tylonolide derivatives and salts thereof as claimed in claim 1 wherein R$^2$ represents hydroxyl and R$^3$ represents hydrogen.

4. Mycaminosyl tylonolide derivatives and salts thereof as claimed in claim 1 wherein R$^2$ represents hydrogen and R$^3$ represents a formyl group.

5. Mycaminosyl tylonolide derivatives and salts thereof as claimed in claim 1 wherein R$^2$ represents hydroxyl are R$^3$ represents a formyl group.

* * * * *